US00PP33002P3

(12) United States Plant Patent
Hand et al.

(10) Patent No.: US PP33,002 P3
(45) Date of Patent: Apr. 27, 2021

(54) ***CANNABIS* PLANT NAMED 'MR2018003'**

(50) Latin Name: *Cannabis sativa*
Varietal Denomination: MR2018003

(71) Applicant: Aurora Cannabis Enterprises Inc., Edmonton (CA)

(72) Inventors: Andrew Hand, Bradford (CA); Alan Graziano, Toronto (CA)

(73) Assignee: Aurora Cannabis Enterprises Inc., Edmonton (CA)

( * ) Notice: Subject to any disclaimer, the term of this patent is extended or adjusted under 35 U.S.C. 154(b) by 0 days.

(21) Appl. No.: 16/602,633

(22) Filed: Nov. 13, 2019

(65) Prior Publication Data

US 2020/0154623 P1 May 14, 2020

(30) Foreign Application Priority Data

Nov. 14, 2018 (CA) ..... PBR 18-9644

(51) Int. Cl.
*A01H 5/02* (2018.01)
*A01H 6/28* (2018.01)
*A61K 36/185* (2006.01)

(52) U.S. Cl.
USPC ..... Plt./258
CPC ..... *A01H 6/28* (2018.05); *A61K 36/185* (2013.01)

(58) Field of Classification Search
USPC ..... Plt./258, 263.1
CPC ... A01H 5/02; A01H 5/00; A01H 5/12; A01H 6/28
See application file for complete search history.

*Primary Examiner* — Kent L Bell
(74) *Attorney, Agent, or Firm* — Christensen O'Connor Johnson Kindness PLLC

(57) ABSTRACT

A new cultivar of *Cannabis* plant named 'MR2019003' that is characterized by an average of 16.77% THC and 0% CBD by dry weight, resistance to microbial growth, high yield and low intra-flower leaves.

3 Drawing Sheets

Genus and species: *Cannabis sativa.*
Variety denomination: 'MR2018003'.

CROSS-REFERENCE TO RELATED APPLICATIONS

This application claims the benefit of priority under 35 U.S.C. 199(f) to Canadian Plant Breeders' Rights Application Number 18-9644, which was filed for the instant plant variety on Nov. 14, 2018.

BACKGROUND OF THE INVENTION

The present invention relates to a new and distinct *Cannabis* (*Cannabis sativa*) cultivar designated as 'MR2018003'.

'MR2018003' is a selection resulting from a controlled-cross made in in Markham, Ontario, Canada, between the female *Cannabis sativa* variety 'Pakistan Chitral Kush Landrace' and the male *Cannabis sativa* variety 'UK Cheese'.

Seeds from the cross were sown in Markham, Ontario, Canada and plants were screened for a number of traits including tetrahydrocannabinol (THC) and cannabidiol (CBD) levels, yield, flowering time, disease resistance and flower morphology. An individual plant having an average of 16.77% THC and 0% CBD by dry weight and have significant resistance to microbial growth was chosen to be 'MR2018003'.

In May 2016, 'MR2018003' was first asexually propagated by apical stem cuttings approximately 10 cm long and having multiple auxiliary meristems, in Markham, Ontario, Canada. 'MR2018003' is stable and reproduces true to type in successive generations of asexual reproduction. This cultivar has increased resistance to microbial growth and higher flower yield for enhanced cultivation and production of flower yield and extracts thereof.

BRIEF SUMMARY OF THE INVENTION

This invention relates to a new and distinctive *Cannabis* cultivar designated as 'MR2018003'.

'MR2018003' exhibits an average of 16.77% THC and 0% CBD by dry weight. 'MR2018003' also exhibits resistance to microbial growth, high yield and a low number of intra-calyx leaves.

BRIEF DESCRIPTION OF THE DRAWINGS

The accompanying color photographs depict characteristics of 'MR2018003'. The colors shown are as true as can be reasonably obtained by conventional photographic procedures. The photographs are of plants aged 8 to 9 weeks post-floral transition and grown in flower rooms under standard cultivation methods in Bradford, Ontario Canada.

DETAILED BOTANICAL DESCRIPTION

Figure 1:
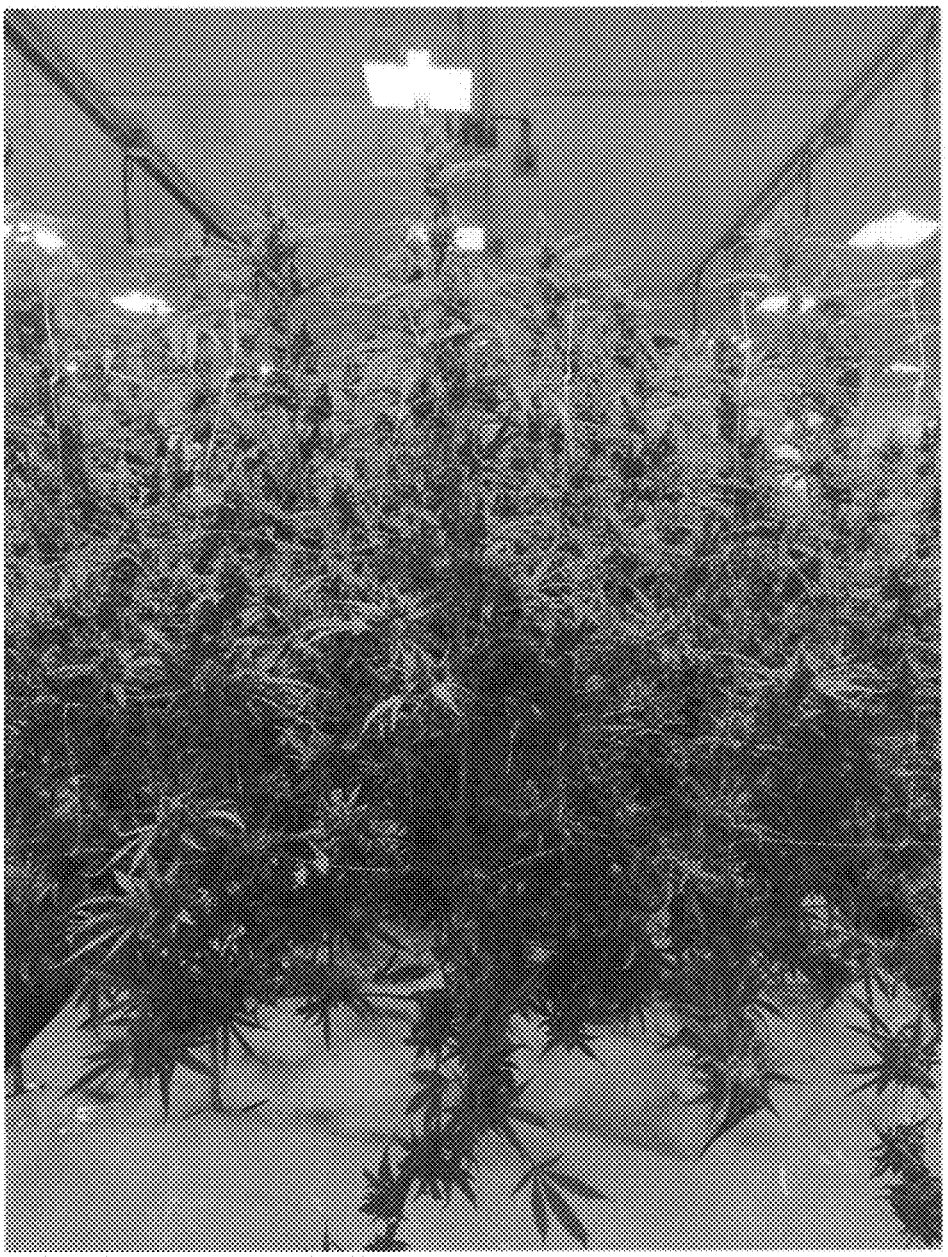
FIG. 1 shows multiple, whole plant clones of 'MR2018003'.
Figure 2:
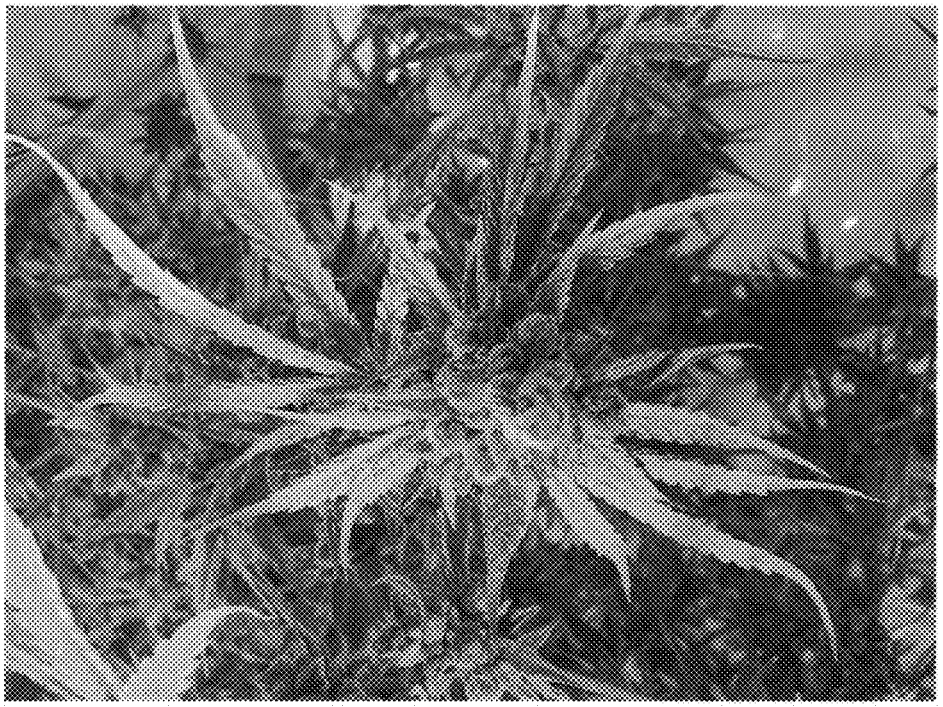
FIG. 2 shows a close-up view of a single inflorescence and foliage of 'MR2018003'.
Figure 3:
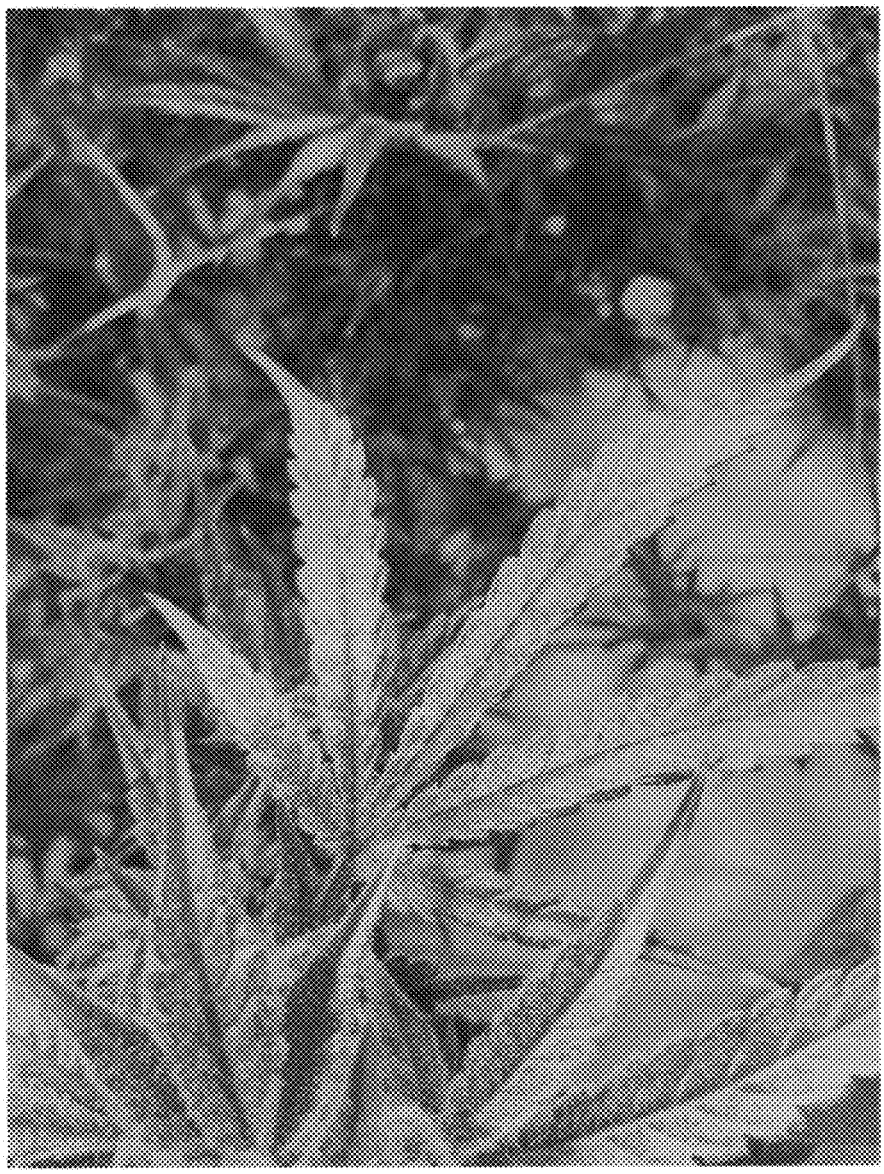
FIG. 3 shows a close-up view of foliage of 'MR2018003'.

The following is a detailed description of the new cultivar 'MR2018003'.

'MR2018003' has not been tested under all possible environmental conditions. Phenotypic differences may be observed with variations in environment without any variance in genotype.

The traits of 'MR2018003' have been repeatedly observed and represent the distinguishing characteristics of 'MR2018003'.

The data that follows was collected in Markham, Ontario Canada and Bradford, Ontario, Canada from plants aged 8 to 9 weeks post-floral transition.

Plants were flowered under standard indoor environmental conditions with High Pressure Sodium lamps. Clones were cut from healthy mothers and allowed to root for 14 to 18 days prior to being introduced to the flower room. The room was maintained at 18 hour days/6 hour nights for a week to allow the cuttings to establish adequate vegetative tissue. The floral transition was initiated by switching to 12 hour days and 12 hour nights. Flowering lasted 9 weeks before harvest, at which point morphological measurements were taken, samples were taken for chemical analysis, and yield was quantified.

Standard in-house developed nutrients were used throughout growth, and the plants were defoliated and pruned as necessary throughout the cycle.

In the following description, the color determination is in accordance with the 2017 Munsell Plant Tissue Color Book, except where general color terms of ordinary dictionary significance are used.

Classification:

*Denomination*.—'MR2018003'.
*Family*.—Cannabacaeae.
*Genus*.—*Cannabis*.
*Species*.—*Cannabis sativa*.
*Common name*.—Marijuana.

Parentage: Female *Cannabis sativa* variety 'Pakistan Chitral Kush Landrace' (unpatented) and male *Cannabis sativa* variety 'UK Cheese' (unpatented).

Propagation: 'MR2018003' is asexually (clonally) propagated from vegetative cuttings. It takes approximately 18 days to produce a rooted young plant. Roots are fine and well-branched.

Plant:

*Average height*.—90.3 cm.
*Width*.—40 cm-55 cm.

Stems:

*Length/height*.—78 cm-110 cm.
*Width/diameter*.—4 mm-9 mm.
*Color*.—2.5 GY 5/6, 5GY 7/8, 5RP 3/4.
*Shape*.—Tubular.
*Texture*.—Fibrous and Pubescent.
*Lateral branch length*.—15 cm-48 cm.
*Average number of nodes*.—29.2.
*Average internodal length*.—6.2 cm.

Foliage:

*Type/form*.—Palmately Compound.
*Arrangement*.—Alternate.
*Attachment*.—Petiolate.
*Leaf width*.—16 cm-18 cm for fully mature leaves.
*Leaf length*.—13 cm-16 cm for fully mature leaves.
*Number of leaflets per leaf*.—5-7.
*Leaflet shape*.—Lanceolate.
*Leaflet length*.—13 cm-14 cm for longer leaflets, and 3 cm-5 cm for shorter leaflets.
*Leaflet width*.—1.5 cm-2.0 cm for larger leaflets, and 0.3 cm-1.0 cm for smaller leaflets.
*Leaflet margin*.—Serrate.
*Leaflet apex*.—Acuminate.
*Leaflet base*.—Attenuate.
*Leaflet color, upper surface*.—5GY 4/4, 7.5 GY 3/4.
*Leaflet color, lower surface*.—7.5 GY 6/8.
*Venation pattern and description, upper and lower leaflet surfaces*.—Pinnate.
*Texture* (*both surfaces*).—Pubescent, primarily on the abaxial side and along leaf vasculature.
*Fragrance*.—Sweet, berry, fruity, cheesy.
*Stipules*.—Present, 2 per node on either side of a petiole, attenuated.

Petiole:

*Length*.—2 cm-6 cm.
*Diameter*.—1.6 mm-2.5 mm.
*Texture*.—Fine, short non-glandular trichomes.
*Color*.—5RP 4/6.

Inflorescence: The plant is a genetically female dioicous plant and, therefore, produces predominantly female flowers. There are no male-only plants. There is a very low incidence of hermaphroditism.

*Blooming habit*.—Short day photoperiod sensitive.
*Blooming period*.—50 days. Male flowering: male flowers are very rare; if present, typically develop between week 2 and 4 of general flowering.
*Attachment*.—Subsessile.
*Bracts*.—Covered with trichomes and resin glands with 2-3 stigmas emerging in each.
*Bract color*.—5RP ¾ (Munsell) (typical and observed).
*Trichomes*.—Capitate-sessile, capitate-stalked, bulbous, and non-glandular (cystolith hairs); trichomes are present on almost all aerial organs but are present at highest concentration on female flowers (including calyxes and bracts) as well as subtending intra-flower leaves.
*Bract trichome and resin gland color*.—Trichomes are clear, and will turn amber (approximately 10R 4/10 (Munsell)) during senescence.
*Fragrance*.—Sweet, berry, and fruity.
*Inflorescence color*.—7.5 GY 5/2.
*Number of inflorescences per plant*.—65-95.
*Diameter*.—3 cm-4.5 cm.
*Length*.—4 cm-7 cm.
*Inflorescence anthocyanin*.—Medium to strong anthocyanin presence. 5 RP 3/2. Male flowers (very rare) do not produce anthocyanin coloration.
*Yield*.—Average flowering yield 609 g/m$^2$ per growing space; average trim yield 333 g/m$^2$.

Reproductive organs:

*Pistils*.—1.
*Quantity* (*of stigmas*) *per flower*.—2-3.
*Stigma color*.—5 YR 5/10 at maturity/senescence; 7.5 GY 7/4 for younger plants.
*Stigma length*.—On average between about 2-5 mm.

Disease and insect/pest resistance: 'MR2018003' exhibits resistance to aerobic bacteria, yeast, mold and coliform bacteria as shown in Table 1.

TABLE 1

| 'MR2018003' resistance to aerobic bacteria, yeast, mold and coliform bacteria. | |
|---|---|
| Average Aerobic Bacteria Count (per plant, in colony forming units (CFUs)) | 145 |
| Average Yeast and Mold Count (per plant, in CFUs) | 37.5 |
| Average coliform bacteria count (per plant, in CFUs) | 32.5 |

COMPARISON WITH PARENTAL LINES AND KNOWN VARIETY

'MR2018003' may be compared with its parental lines with respect to THC content. Using Waters LC-MS/MS, running an Acetonitrile:Methanol:2-propanol gradient mobile phase through a Raptor ACR-18, 2.7 um, 2.1×150 mm column to quantify THC and CBD, 'MR2018003' exhibits an average of 16.77% THC by dry weight, the female parent exhibits 12% THC by dry weight and the male parent exhibits 16% THC by dry weight.

The closest variety of *Cannabis* known to the inventors is the commercial variety 'Girl Scout Cookies'. 'MR2018003' can be distinguished from 'Girl Scout Cookies' by its increased resistance to microbial growth, as shown in Table 2.

TABLE 2

Comparison between 'MR2018003' and 'Girl Scout Cookies': Microbial resistance

| Variety | # of Cycles Grown | Average Aerobic Bacteria Count* | Average Yeast and Mold Count** | Average Coliform Bacteria Count* |
|---|---|---|---|---|
| 'MR2018003' | 5 | 145 | 37.5 | 32.5 |
| 'Girl Scout Cookies' | 15 | 59270 | 52450 | 760 |

**Aerobic Bacteria Count, Yeast and Mold Count and Coliform Bacteria Count were determined per plant, in colony forming units (CFUs).

Variety 'MR2018003' can also be distinguished from the variety 'Girl Scout Cookies' with respect to the morphological traits shown the Table 3.

TABLE 3

Comparison between 'MR2018003' and 'Girl Scout Cookies': Morphological traits

| Characteristic | MR2018003 | 'Girl Scout Cookies' |
|---|---|---|
| Overage Average Height | 87.9 cm | 69.6 cm |
| Average Height | 90.3 cm | 74 cm |
| Average # of Nodes | 29.2 | 22.3 |
| Average Internodal Length | 6.2 cm | 6.6 cm |
| Average Flower Width | 3.4 cm | 5.3 cm |

'MR2018003' also has a higher yield and fewer intra-flower leaves than 'Girl Scout Cookies'. The flowers of 'MR2018003' are dark purple in colour and have large, swollen calyxs. In contrast, the flowers of 'Girl Scout Cookies' are green in colour and the calyxs are not as large.

The invention claimed is:

1. A new and distinct cultivar of *Cannabis* plant named 'MR2018003' as described and illustrated herein.

* * * * *